United States Patent [19]

Tamaru et al.

[11] Patent Number: 5,268,521
[45] Date of Patent: Dec. 7, 1993

[54] CATALYST FOR SELECTIVE HYDROGENATION REACTION

[75] Inventors: Kenji Tamaru, Kamakura; Kikuo Shoji; Kazuki Noda, both of Tokyo, all of Japan

[73] Assignee: Tanaka Kikinzoku Kogyo K.K., Japan

[21] Appl. No.: 799,738

[22] Filed: Nov. 22, 1991

Related U.S. Application Data

[63] Continuation of Ser. No. 694,362, May 1, 1991, abandoned.

[51] Int. Cl.$^5$ .............................................. C07C 5/05
[52] U.S. Cl. ................................. 585/273; 585/275; 585/277
[58] Field of Search .................... 585/273, 275, 277

[56] References Cited

U.S. PATENT DOCUMENTS

| | | | |
|---|---|---|---|
| 2,842,504 | 7/1958 | Jones | 502/159 |
| 3,346,482 | 10/1967 | Arey, Jr. et al. | 502/74 |
| 3,396,123 | 8/1968 | Urban | 502/159 |
| 4,560,817 | 12/1985 | Bobsein et al. | 585/275 |

FOREIGN PATENT DOCUMENTS 27137 2/1982 Japan .................................. 502/159

*Primary Examiner*—Patrick P. Garvin
*Assistant Examiner*—E. D. Irzinski
*Attorney, Agent, or Firm*—Klauber & Jackson

[57] ABSTRACT

Disclosed herein is a catalyst for especially for selective hydrogenation among a carbon-carbon double bond, a carbonyl group and an aromatic unsaturated ring such as benzene. The catalyst comprising platinum and zeolite can be employed for selectively hydrogenating the carbon-carbon double bond and the carbonyl group of an organic compound without the hydrogenation of the aromatic unsaturated. The catalyst comprising the platinum supported on a support which comprises powders of an inorganic component to which is supported polyethylene glycol or an ethylvinylbenzene-divinylbenzene copolymer can be employed for selectively hydrogenating the carbon-carbon double bond of an organic compound without the hydrogenation of the carbonyl group and the aromatic unsaturated ring.

3 Claims, 3 Drawing Sheets

HYDROGENATION OF THE MIXTURE OF MVK AND TOLUENE OVER Pt/PEG AT 60°C. SOLVENT: ACETIC ACID

○ MVK  ● MEK  △ 2-BUTANOL  □ TOLUENE
■ METHYLCYCLOHEXANE

HYDROGENATION OF THE MIXTURE OF MVK AND TOLUENE OVER Pt/PORAPAK Q AT 60°C. SOLVENT: n-HEXANE

○ MVK  ● MEK  △ 2-BUTANOL  □ TOLUENE
■ METHYLCYCLOHEXANE

HYDROGENATION OF THE MIXTURE OF MVK AND TOLUENE
OVER Pt/CARBON AT 60°C.   SOLVENT: n-PENTANOL

○ MVK   ● MEK   △ 2-BUTANOL   □ TOLUENE
■ METHYLCYCLOHEXANE

HYDROGENATION OF THE MIXTURE OF MVK AND TOLUENE
OVER Pt/Al$_2$O$_3$ AT 60°C.   SOLVENT: n-HEXANE

○ MVK   ● MEK   △ 2-BUTANOL   □ TOLUENE
■ METHYLCYCLOHEXANE

HYDROGENATION OF THE MIXTURE OF MVK AND TOLUENE
OVER Pt/PORAPAK Q AT 60°C.   SOLVENT: n-PENTANOL

○ MVK   ● MEK   △ 2-BUTANOL   □ TOLUENE
■ METHYLCYCLOHEXANE

CATALYST FOR SELECTIVE HYDROGENATION REACTION

CROSS-REFERENCE TO RELATED APPLICATIONS

This application is a continuation of U.S. application Ser. No. 07/694,362 filed on May 1, 1991, now abandoned, priority of which is claimed hereunder.

BACKGROUND OF INVENTION

1. Technical Field

This invention relates to a catalyst for selective hydrogenation of an organic compound for selectively conducting a catalytic hydrogenation reaction for an organic compound having various functional groups such as a carbon-carbon double bond, a carbonyl group and an aromatic unsaturated ring.

2. Background Art

Heretofore, as a selective hydrogenation reaction catalyst, platinum and palladium which are supported on a heat stable support such as alumina, carbon, silica and the like are employed.

However, these catalysts have the problems that the catalyst support itself may affect the reaction and the selectivity of the hydrogenation reaction of an aromatic unsaturated ring such as benzene is quite unstable.

Such problems are pointed out that the large change of activity of a catalyst occurs when an active metal such as platinum is dispersed on the thermally stable support, and the selectivity of a catalyst reaction remarkably differs depending on the supporting ratio of the platinum even if the support is the same, so that the selectivity of the catalyst is controlled by the addition of a poisoned metal.

There are three kinds of functional groups of an organic compound that may be hydrogenated, that is, a carbon-carbon double bond, a carbonyl group and an aromatic unsaturated ring. The resistance to hydrogenation increases in this turn.

Therefore, the selective hydrogenation means that only the double bond or the double bond and the carbonyl group are hydrogenated. In organic synthesis or the like, the increase of selectivity is quite important for maximizing the total yield.

Heretofore, researchers have endeavored themselves to develop a highly selective catalyst for the hydrogenation reactions to obtain only the above mentioned limited results.

SUMMARY OF THE INVENTION

An object of the present invention is to provide a catalyst for selective hydrogenation especially among a carbon-carbon double bond, a carbonyl group and an aromatic unsaturated which overcomes the above mentioned drawbacks.

Another object of the invention is to provide a catalyst for a selective hydrogenation reaction capable of selectively carrying out a catalytic hydrogenation reaction by exerting a catalytic effect on specific functional groups among various unsaturated functional groups of an organic compound as mentioned above.

One aspect of the present invention is, in a catalyst for a selective hydrogenation reaction which exerts a catalytic effect on a carbon-carbon double bond and a carbonyl group and does not exert on an aromatic unsaturated ring of an organic compound, the catalyst comprises platinum supported on zeolite.

Another aspect of the invention is, in a catalyst for a selective hydrogenation reaction which exerts a catalytic effect on a carbon-carbon double bond and does not exert on a carbonyl group and an aromatic unsaturated ring of an organic compound, the catalyst comprises platinum supported on a support which comprises powders or particles of an inorganic component on which is supported polyethylene glycol or an ethylvinylbenze-divinylbenze copolymer.

The selectivity of the catalyst may be influenced by a solvent employed in a hydrogenation reaction.

DETAILED DESCRIPTION OF INVENTION

Figure 1:
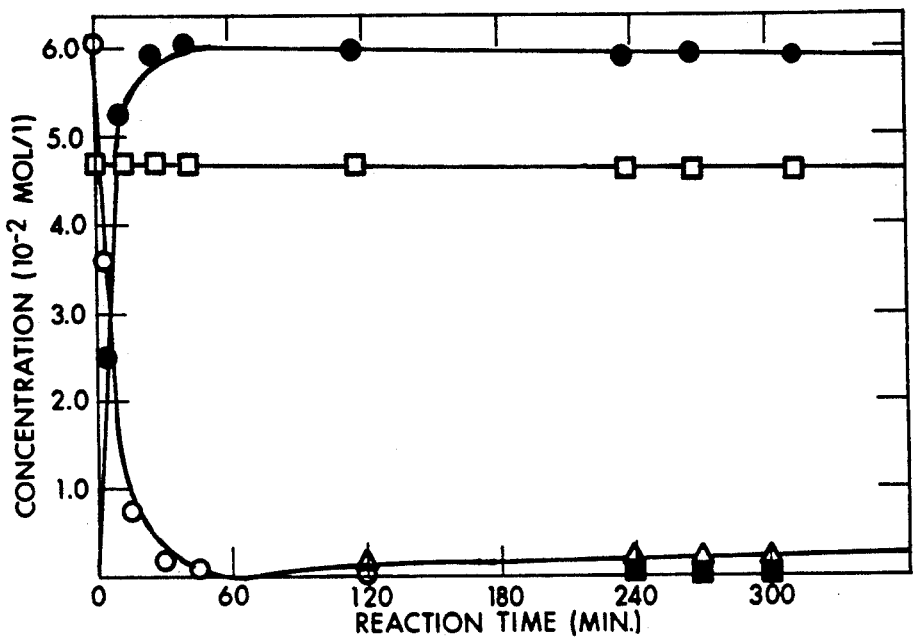
FIG. 1 is a graph showing the relation between a reaction time and concentrations of MVK, MEK, 2-butanol, toluene and methylcyclohexane in the hydrogenation reaction of MVK and the toluene employing a catalyst of Example 2.

When an organic compound containing two or more unsaturated functional groups is hydrogenated employing a catalyst of this invention, selective hydrogenation can be conducted.

An example of a hydrogenation reaction of a carbon-carbon double bond is conversion of methyl vinyl ketone (hereinafter referred to as MVK) into methyl ethyl ketone (hereinafter referred to as MEK) through a hydrogenation reaction of the carbon-carbon double bond. An example of a hydrogenation reaction of a carbonyl group is conversion of the MEK to 2-butanol through a hydrogenation reaction of the carbonyl group. An example of a hydrogenation reaction of an aromatic unsaturated ring is conversion of toluene to methylcyclohexane through a hydrogenation reaction of the benzene ring. The aromatic unsaturated ring of this invention includes a five-membered or six-membered conjugated organic compound such as benzene, toluene, pyridine, pyrazole and furan and its fused ring compound such as naphthalene.

As described, when the hydrogenation is carried out employing the first catalyst comprising the zeolite and the platinum supported thereon, the carbon-carbon double bond and the carbonyl group of an organic compound can be hydrogenated without the hydrogenation of the aromatic unsaturated ring. When the hydrogenation is carried out employing the second catalyst comprising the platinum supported on a support which may comprise powders of which a main component is silica or other inorganic components to which is supported polyethylene glycol or an ethylvinylbenze-divinylbenze copolymer, the carbon-carbon double bond of an organic compound can be hydrogenated without the hydrogenation of the carbonyl group and the aromatic unsaturated ring. However, the selectivity may be influenced by a solvent employed in the hydrogenation reaction. While, for example, the ethylvinylbenze-divinylbenze copolymer catalyst selectively hydrogenates the carbon-carbon double bond in n-hexane, the catalyst hydrogenates the carbonyl group in addition to the carbon-carbon double bond in n-pentanol.

The catalyst is quite effective for selective hydrogenation of an organic compound which contains the above-mentioned two or more groups. Even if an $\alpha\text{-}\beta$ unsaturated carbonyl group is hydrogenated employing the second catalyst, only the carbon-carbon double bond can be selectively hydrogenated.

The above two catalysts can be prepared according to a conventional method such as a thermal decomposition method and an ion exchange method.

Examples of the catalysts of the present invention will be described, but they do not intend to restrict the present invention.

EXAMPLE 1

A support was prepared by means of an ion exchange method by applying an aqueous solution of tetraamine platinum dichloride $[Pt(NH_3)_4]Cl_2$ onto 7 g of powdered zeolite (NaY type). The supporting rate of the platinum was made to be 3.0 weight %.

EXAMPLE 2

A support was employed which was prepared by supporting 20 weight % of polyethylene glycol having average molecular weight of 40,000 on white kieselguhr. After platinum was adsorbed on the support by means of an impregnation method employing an acetone solution of chloroplatinic acid ($H_2PtCl_4$), it was dried and then reduced in a hydrogen stream at a room temperature for three hours and at 200° C. for three hours to prepare a platinum catalyst. The supporting rate of the platinum was made to be 5.0 weight %.

EXAMPLE 3

After platinum was adsorbed on 7 g of powdery Porapak Q (tradename, ethylvinylbenzene-divinylbenzene copolymer, 50 to 80 mesh) employed as a support by means of an impregnation method employing an acetone solution of chloroplatinic acid ($H_2PtCl_4$), it was dried and then reduced in a hydrogen stream at a room temperature for three hours and at 200° C. for three hours to prepare a platinum catalyst. The supporting rate of the platinum was made to be 5.0 weight %.

COMPARATIVE EXAMPLE 1

After platinum was adsorbed on 7 g of powdery alumina ($Al_2O_3$, 60 to 80 mesh) employed as a support by means of an impregnation method employing an acetone solution chloroplatinic acid ($H_2PtCl_4$), it was dried and then reduced in a hydrogen stream at a room temperature for three hours and at 200° C. for three hours to prepare a platinum catalyst. The supporting rate of the platinum was made to be 5.0 weight %.

COMPARATIVE EXAMPLE 2

A platinum catalyst was prepared under the same conditions as those of Comparative Example 1 except that powdery carbon was employed in place of the powdery alumina.

Hydrogenation reactions were carried out under atmospheric pressure at 60° C. in a rotation-mix-type liquid phase reaction apparatus of which an inner volume was 500 ml and in which 50 ml of a solvent containing 0.0061 mol of MVK (an organic compound having a carbon-carbon double bond and a carbonyl group) and 0.0047 mol of toluene (an organic compound having a benzene ring) as hydrogenation reaction substances was supplied. The respective five platinum catalysts prepared in the Examples 1, 2 and 3 and the Comparative Examples 1 and 2 were separately introduced in the reaction apparatus. The solvents employed were acetic acid (Examples 1 and 2), n-hexane (Example 3 and Comparative Example 1) and n-pentanol (Comparative Example 2).

The composition of the reacted solution was analyzed by gas chromatography.

In the respective all reactions, the carbon-carbon double bonds of MVK were preferentially hydrogenated so that all MVK was rapidly converted to MEK in 15 to 45 minutes.

On the other hand, the selectivity of the hydrogenation reaction of the carbonyl group and the benzene ring considerably differed depending on the kind of a catalyst support. In the reaction employing the catalyst having the zeolite, the hydrogenation of the benzene ring did not proceed. In the reaction employing the catalysts having the polyethylene glycol containing support, the hydrogenation of the carbonyl group and the benzene ring did not proceed.

The results of the reactions are shown in the graphs of the attached drawings.

Although the result is not shown in a graph, the catalyst of Example 1 exhibited excellent selectivity to almost selectively produce 2-butanol. Toluene was not hydrogenated.

As shown in FIG. 1, in the hydrogenation reaction employing the catalyst of Example 2, MVK was completely hydrogenated to MEK in 60 minutes without further hydrogenated product, 2-butanol. Therefore, the catalyst containing polyethylene glycol was highly selective for a carbon-carbon double bond.

Figure 2:
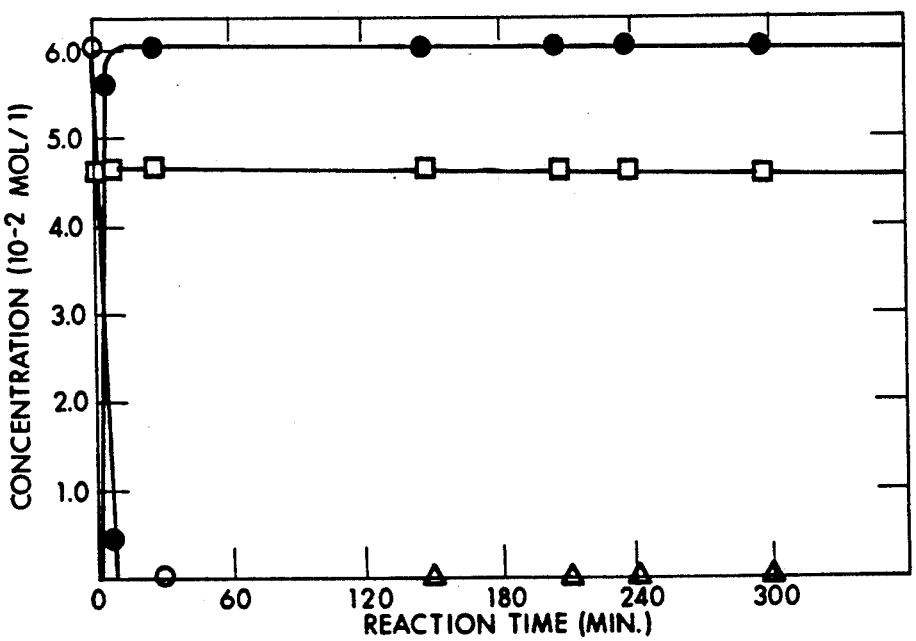
FIG. 2 is a graph showing the relation between a reaction time and concentrations of the compounds of FIG. 1 employing a catalyst of Example 3.
Figure 5:
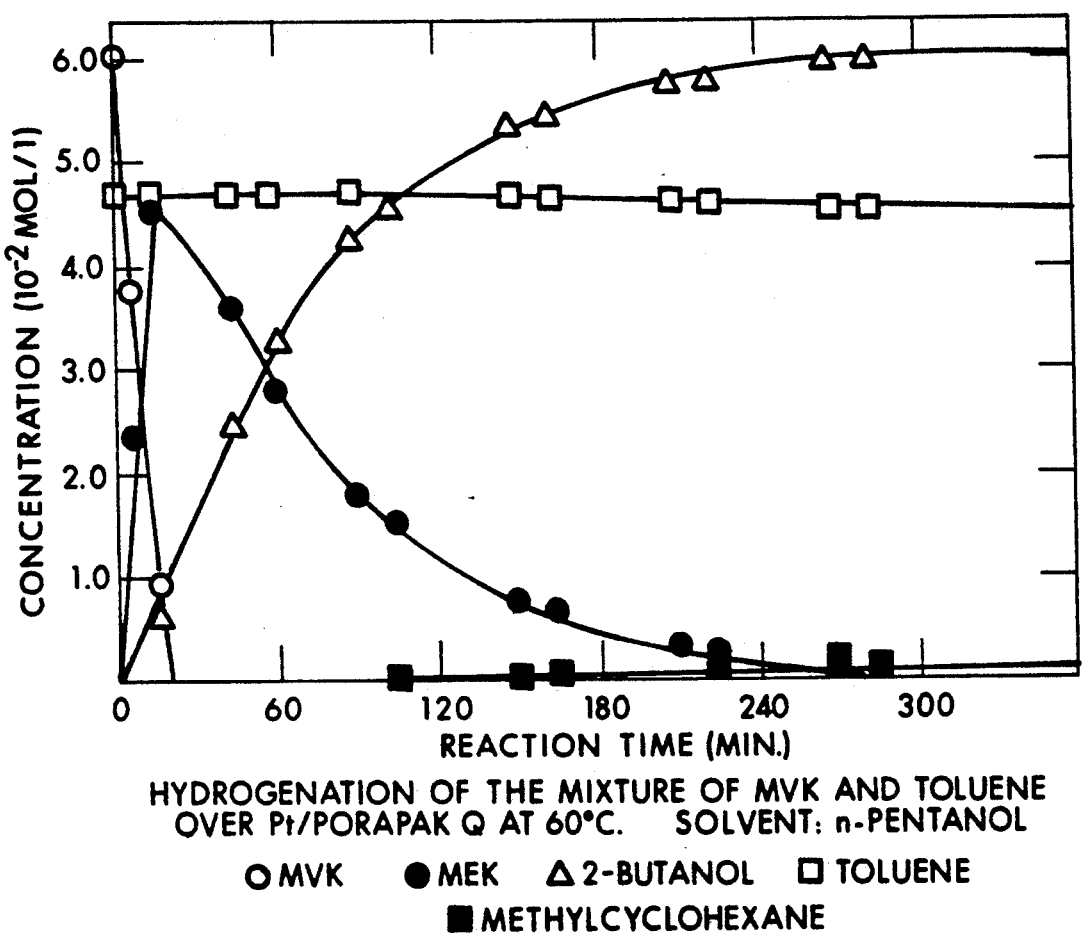
FIG. 5 is a graph showing the relation between a reaction time and concentrations of the compounds of FIG. 1 employing a catalyst of Example 3 and 2-pentanol as a solvent in place of n-hexane.

As shown in FIG. 2, in the hydrogenation reaction employing the catalyst of Example 3, MVK was also completely hydrogenated to MEK in 15 minutes without further hydrogenated product, 2-butanol. Therefore, the catalyst containing the ethylvinylbenzene-divinylbenzene copolymer was highly selective for a carbon-carbon double bond in n-hexane. However, as shown in FIG. 5, MVK was hydrogenated not only to MEK but also to 2-butanol in n-pentanol. This fact suggests that the selectivity may depend on a support.

Figure 3:
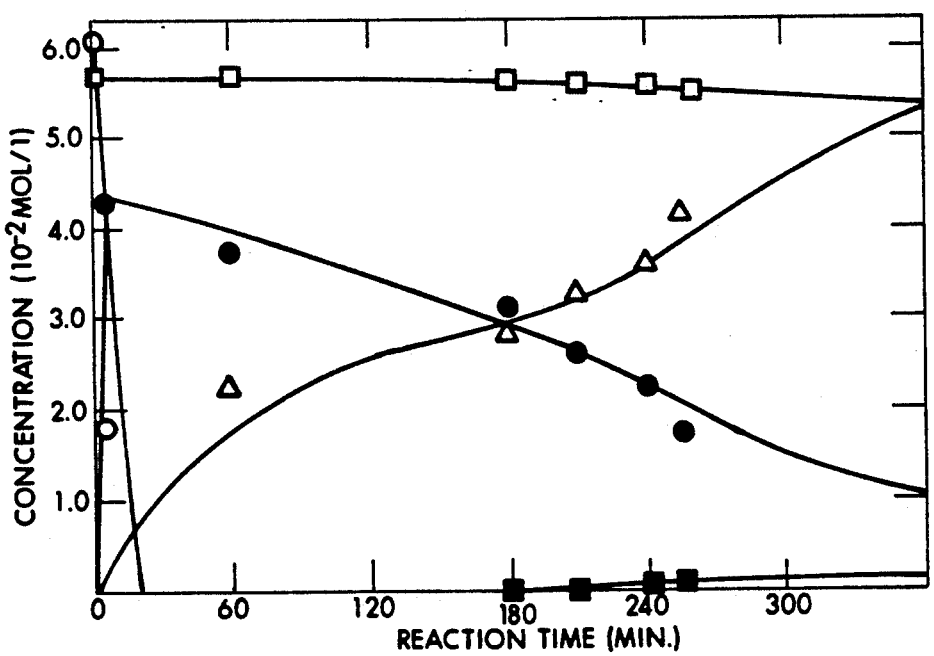
FIG. 3 is a graph showing the relation between a reaction time and concentrations of the compounds of FIG. 1 employing a catalyst of Comparative Example 1.

As shown in FIG. 3, in case of the alumina-support catalyst, MEK and 2-butanol were produced even at an initial stage by the hydrogenation of MVK.

Figure 4:
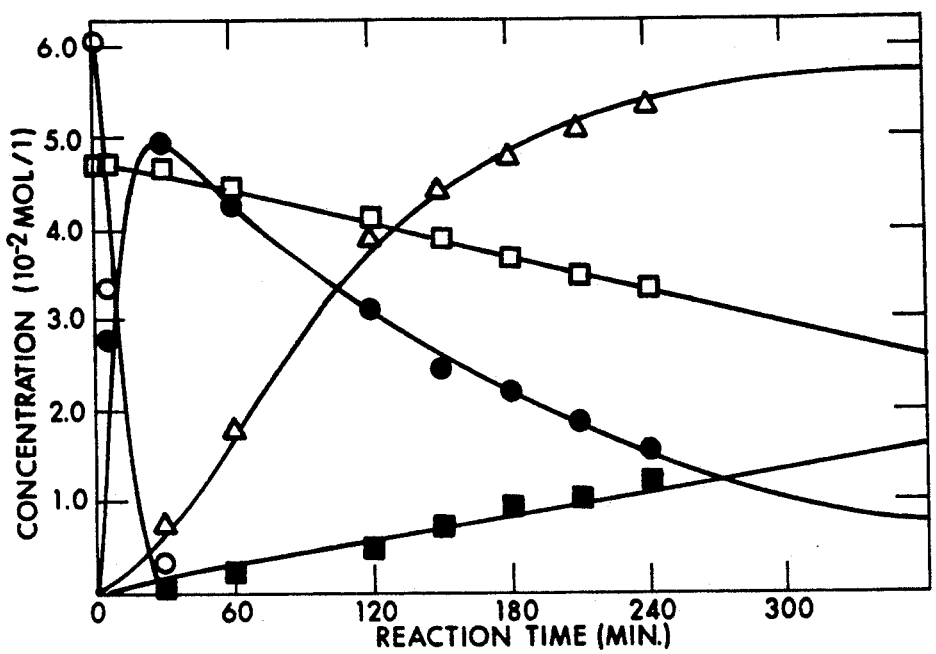
FIG. 4 is a graph showing the relation between a reaction time and concentrations of the compounds of FIG. 1 employing a catalyst of Comparative Example 2.

As shown in FIG. 4, in case of the carbon-support catalyst, methylcyclohexane was produced in addition to MEK and 2-butanol even at an initial stage by the hydrogenation of MVK.

Although the present invention has been described in connection with the Examples, it is readily understood that the present invention is not restricted to the Examples and that various changes and modifications can be made by those skilled in the art without departing from the spirit and scope of the present invention.

What is claimed is:

1. A method for selectively reducing a carbon-carbon double bond or a carbonyl group in an organic compound without substantially hydrogenating an aromatic unsaturated ring of the organic compound, said method comprising the step of catalytically hydrogenating said organic compound in the presence of a catalyst comprised of platinum supported on a substrate comprised of zeolite.

2. A method for selectively reducing a carbon-carbon double bond in an organic compound without substantially hydrogenating a carbonyl group and an aromatic unsaturated ring of the organic compound, said method comprising the step of catalytically hydrogenating said organic compound in the presence of a catalyst comprised of platinum supported on a support, comprised of a member selected from the group consisting of polyethylene glycol on a powder or particle substrate, and ethylvinylbenzene-divinylbenzene copolymer on a powder or particle substrate.

3. The method of claim 2 wherein each powder or particle substrate is comprised of kieselguhr.